United States Patent
West

(10) Patent No.: US 6,746,523 B1
(45) Date of Patent: Jun. 8, 2004

(54) METAL SALT-FATTY AMINE COMPLEX WOOD PROTECTION

(76) Inventor: Michael Howard West, 54 S. Crockett Rd., Senatobia, MS (US) 38668

( * ) Notice: Subject to any disclaimer, the term of this patent is extended or adjusted under 35 U.S.C. 154(b) by 0 days.

(21) Appl. No.: 10/412,489

(22) Filed: Apr. 14, 2003

(51) Int. Cl.$^7$ ................................................ A01N 33/02
(52) U.S. Cl. .................... 106/18.32; 424/617; 424/618; 424/639; 424/646; 424/647; 514/492; 514/501; 514/502
(58) Field of Search ........................ 106/18.32; 424/617, 424/618, 639, 646, 647; 514/492, 501, 502

(56) References Cited

U.S. PATENT DOCUMENTS

| | | | | |
|---|---|---|---|---|
| 3,391,127 A | * | 7/1968 | Kamal | 528/9 |
| 4,086,066 A | * | 4/1978 | McDermott | 44/357 |
| 4,357,163 A | * | 11/1982 | Amundsen et al. | 106/18.35 |
| 4,379,810 A | * | 4/1983 | Amundsen et al. | 428/541 |
| 4,382,105 A | * | 5/1983 | Amundsen et al. | 427/370 |
| 4,461,721 A | * | 7/1984 | Goettsche et al. | 252/607 |
| 6,547,864 B1 | * | 4/2003 | West | 106/18.32 |
| 6,579,354 B1 | * | 6/2003 | West | 106/18.32 |
| 6,623,552 B1 | * | 9/2003 | West | 106/18.32 |

* cited by examiner

Primary Examiner—Anthony J. Green

(57) ABSTRACT

A composition for protecting wood from weathering which comprises the complex from an acidic water soluble metal salt combined with fatty amine in a weight ratio of from 1 to 10 to 10 to 1 metal salt to fatty amine wherein the metal salt is chosen from the group comprising cobalt, iron, manganese, nickel, and silver. The composition may contain a nonionic or cationic pesticide.

3 Claims, No Drawings

METAL SALT-FATTY AMINE COMPLEX WOOD PROTECTION

CROSS REFERENCE TO RELATED APPLICATIONS—NOT APPLICABLE

STATEMENT REGARDING FEDERALLY SPONSORED RESEARCH OR DEVELOPMENT

NOT APPLICABLE

REFERENCE TO A MICROFICHE APPENDIX— NOT APPLICABLE

BACKGROUND OF THE INVENTION

The field of endeavor to which this invention pertains relates to the preparation and use of fatty amine—acidic water soluble metal salt complexes for wood weathering protection wherein the metal salt is chosen from cobalt, iron, manganese, nickel, and silver. My invention replaces chromium for weathering protection and solves serious chromium environmental problems. In the practice of my invention alkaline fatty amines are neutralized by acidic metal salts rendering the fatty amines water soluble; and reducing the acute hazards of both fatty amine and metal salt. The compositions of my invention should be used in aqueous dilution for wood treatment. Pesticides and other ingredients can be used with my composition so long as they are not alkaline and not anionic.

BRIEF SUMMARY OF THE INVENTION

The substance of the claimed invention relates to a composition for protecting wood from weathering which comprises an acidic water soluble metal salt combined with fatty amine in a weight ratio of from 1 to 10 to 10 to 1 metal salt to fatty amine wherein the metal salt is chosen from the group comprising cobalt, iron, manganese, nickel, and silver. The substance also includes the use of acidic or neutral cationic or nonionic pesticides with the composition of my invention.

DETAILED DESCRIPTION OF THE INVENTION

My preferred embodiment employs aqueous concentrates of cobaltous nitrate, ferric nitrate, manganese nitrate, nickel nitrate, and silver nitrate with technical dimethylcocoamine in about a 1 to 1 weight ratio. The aqueous combination should be blended until the fatty amine is thoroughly dispersed, then the complex should be diluted to about a 1 to 10% concentration in water for wood treating. Use the lower concentrations for pressure applications, and the higher levels for superficial treatments. A 5% complex concentration according to my preferred embodiment using each of the metal nitrates was used to brush coat pine boards then compared to untreated controls when exposed to weathering for one year. After the test period the treatments using my composition exhibited little weathering while the controls were badly weathered.

It will be obvious to those skilled in the art that metal salts in combination often exhibit improved wood protection, and the degree of improvement can be determined by simple experimentation. It will also be apparent that compatible pesticides may be vastly improved by combining them with my composition. This, again, can be confirmed by simple experimentation.

I claim:

1. A composition for protecting wood from weathering which comprises the complex from an acidic water soluble metal salt combined with fatty amine in a weight ratio of from 1 to 10 to 10 to 1 metal salt to fatty amine wherein the metal salt is selected from the group consisting of cobalt, iron, manganese, and silver.

2. A composition for protecting wood from weathering which comprises the complex from an acidic water soluble iron salt combined with fatty amine in a weight ratio of from 1 to 10 to 10 to 1 iron salt to fatty amine, and a nonionic pesticide.

3. A composition for protecting wood from weathering which comprises the complex from an acidic water soluble iron salt combined with fatty amine in a weight ratio of from 1 to 10 to 10 to 1 iron salt to fatty amine, and a cationic pesticide.

* * * * *